US006883522B2

(12) United States Patent
Spence et al.

(10) Patent No.: US 6,883,522 B2
(45) Date of Patent: Apr. 26, 2005

(54) HEART VALVE AND APPARATUS FOR REPLACEMENT THEREOF

(75) Inventors: Paul A. Spence, 5818 Orion Rd., Louisville, KY (US) 40222; Mark Ortiz, Milford, OH (US)

(73) Assignee: Paul A. Spence, Louisville, KY (US)

( * ) Notice: Subject to any disclaimer, the term of this patent is extended or adjusted under 35 U.S.C. 154(b) by 124 days.

(21) Appl. No.: 10/716,844

(22) Filed: Nov. 19, 2003

(65) Prior Publication Data

US 2004/0106990 A1 Jun. 3, 2004

Related U.S. Application Data

(60) Continuation of application No. 09/951,362, filed on Sep. 13, 2001, now abandoned, which is a division of application No. 09/310,891, filed on May 12, 1999, now Pat. No. 6,309,417.

(51) Int. Cl.[7] .............................. A61B 19/00; A61F 2/24
(52) U.S. Cl. ....................................... 128/898; 623/2.11
(58) Field of Search ................. 128/898; 623/2.11–2.13

(56) References Cited

U.S. PATENT DOCUMENTS

| 3,570,014 A | 3/1971 | Hancock ............................. 3/1 |
| 3,579,642 A | 5/1971 | Heffeman et al. .................. 3/1 |
| 3,714,671 A | 2/1973 | Edwards et al. .................... 3/1 |
| 4,035,849 A | 7/1977 | Angell et al. .................... 3/1.5 |
| 4,185,636 A | 1/1980 | Gabbay et al. .............. 128/334 |
| 4,259,753 A | 4/1981 | Liotta et al. ..................... 3/1.5 |
| 4,470,157 A | 9/1984 | Love .............................. 3/1.5 |
| 4,605,407 A | 8/1986 | Black et al. .................... 623/2 |
| 4,705,516 A | 11/1987 | Barone et al. ................. 623/2 |
| 4,851,000 A | 7/1989 | Gupta ............................ 623/2 |
| 5,032,128 A | 7/1991 | Alonso .......................... 623/2 |
| 5,080,669 A | 1/1992 | Tascon et al. ................. 623/2 |
| 5,089,015 A | 2/1992 | Ross ............................. 623/2 |

(Continued)

OTHER PUBLICATIONS

Dr. Giovanni Battista Luciani et al., *Midterm Results After Aortic Valve Replacement with Freehand Stentless Xenografts; A Comparison of Three Prostheses*, Article, pp. 1287–1297, 1998.

Dr. Paolo Bertolini et al., *Aortic Valve Replacement With the Biocor PSB Stentless Xenograft*, Article, pp. 425–430, 1998.

Dr. Xu Y. Jin et al., *Fifth–Year Hemodynamic Performance of the Prima Stentless Aortic Valve*, Article, pp. 805–809, 1998.

Medtronic, Inc., *The Freestyle® Aortic Root Bioprosthesis*, Brochure, 1999.

*Primary Examiner*—David J. Isabella
(74) *Attorney, Agent, or Firm*—Wood, Herron & Evans, L.L.P.

(57) ABSTRACT

Apparatus and methods for replacing a heart valve within a vessel. The apparatus includes a replacement heart valve and a plurality of commisure stabilizers connected to the commisures of the heart valve in a removable manner. The commisure stabilizers position and stabilize the commisures in the proper positions as the replacement heart valve is secured within the vessel. The commisure stabilizers may be removed following securement of the replacement heart valve within the vessel. An expansion or retraction device of the invention assists in properly positioning the valve within the vessel.

3 Claims, 9 Drawing Sheets

U.S. PATENT DOCUMENTS

| | | | |
|---|---|---|---|
| 5,147,391 A | 9/1992 | Lane | 623/2 |
| 5,156,621 A | 10/1992 | Navia et al. | 623/2 |
| 5,163,955 A | 11/1992 | Love et al. | 623/2 |
| 5,197,979 A | 3/1993 | Quintero et al. | 623/2 |
| 5,326,370 A | 7/1994 | Love et al. | 623/2 |
| 5,326,371 A | 7/1994 | Love et al. | 623/2 |
| 5,336,258 A | 8/1994 | Quintero et al. | 623/2 |
| 5,360,014 A | 11/1994 | Sauter et al. | 128/774 |
| 5,476,510 A | 12/1995 | Eberhardt et al. | 623/2 |
| 5,489,297 A | 2/1996 | Duran | 623/2 |
| 5,509,930 A | 4/1996 | Love | 623/2 |
| 5,545,215 A | 8/1996 | Duran | 623/2 |
| 5,584,879 A | 12/1996 | Reimold et al. | 623/2 |
| 5,607,393 A | 3/1997 | Ensminger et al. | 604/93 |
| 5,612,885 A | 3/1997 | Loe | 364/468.04 |
| 5,669,919 A | 9/1997 | Sanders et al. | 606/148 |
| 5,683,402 A | 11/1997 | Cosgrove et al. | 606/150 |
| 5,713,953 A | 2/1998 | Vallana et al. | 623/2 |
| 5,716,399 A | 2/1998 | Love | 623/2 |
| 5,716,401 A | 2/1998 | Eberhardt et al. | 623/2 |
| 5,716,417 A | 2/1998 | Girard et al. | 623/900 |
| 5,728,152 A | 3/1998 | Mirsch, II et al. | 623/2 |
| 5,728,153 A | 3/1998 | Menkis et al. | 523/2 |
| 5,755,783 A | 5/1998 | Stobie et al. | 623/2 |
| 5,766,240 A | 6/1998 | Johnson | 623/2 |
| 5,792,217 A | 8/1998 | Camps et al. | 607/119 |
| 5,800,531 A | 9/1998 | Cosgrove et al. | 623/2 |
| 5,824,068 A | 10/1998 | Bugge | 623/2 |
| 5,855,602 A | 1/1999 | Angell | 623/2 |
| 5,876,436 A | 3/1999 | Vanney et al. | 623/2 |

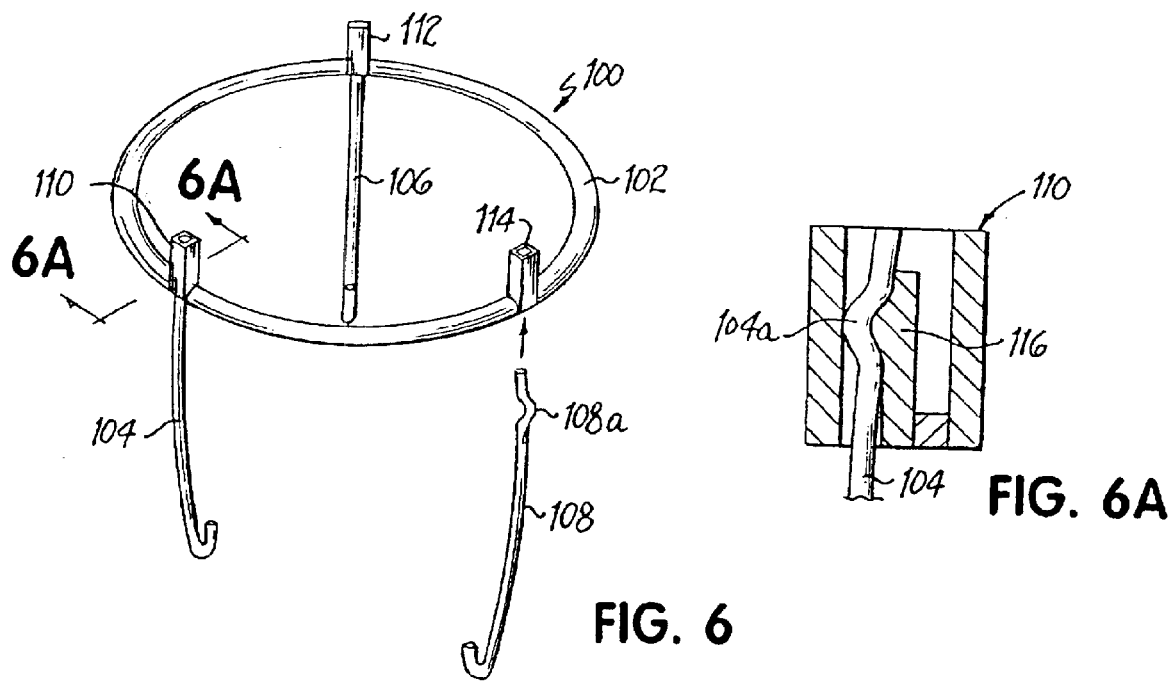
FIG. 6
FIG. 6A
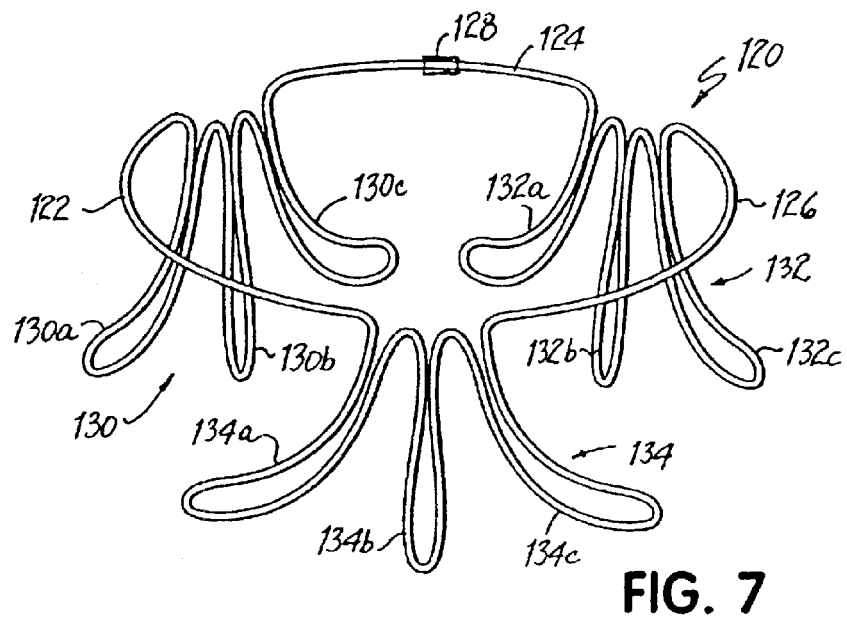
FIG. 7

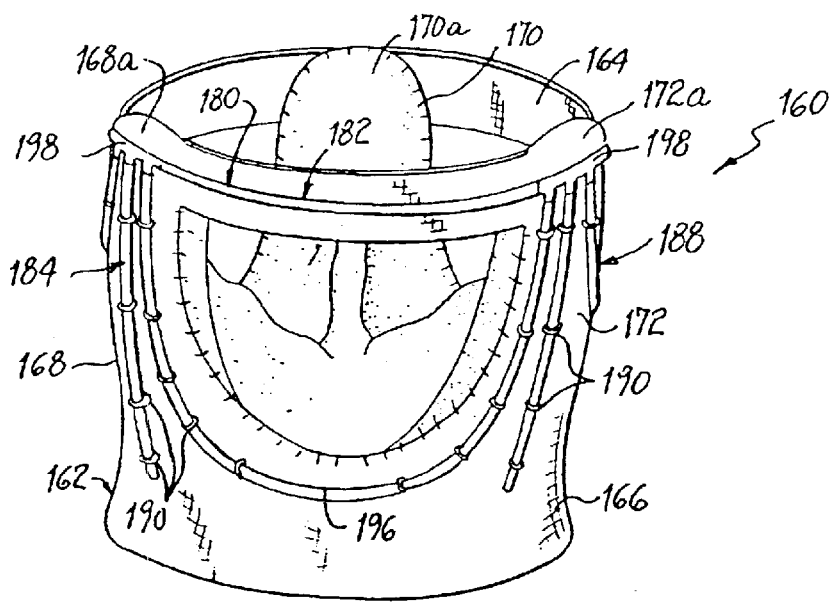
FIG. 9
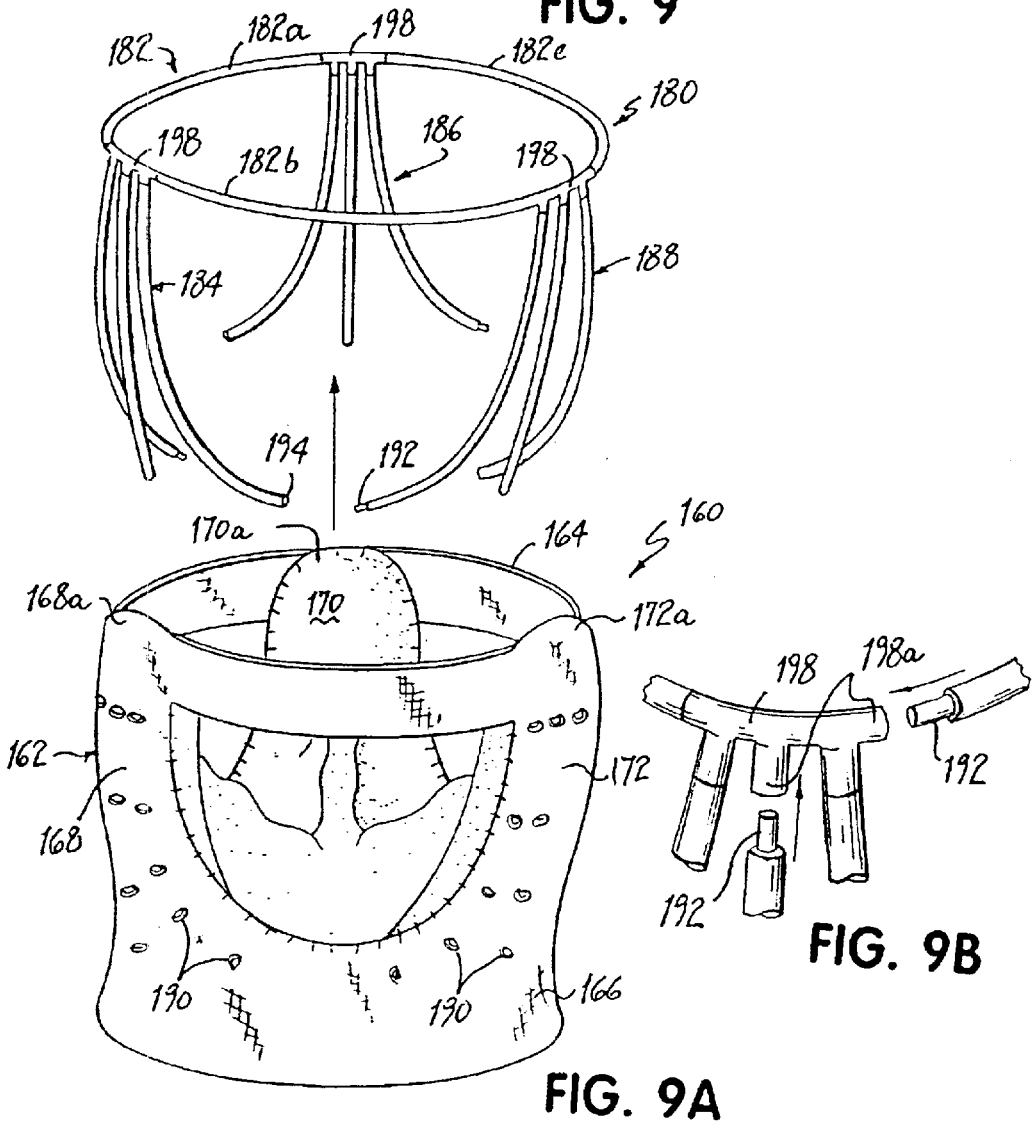
FIG. 9B
FIG. 9A

HEART VALVE AND APPARATUS FOR REPLACEMENT THEREOF

This application is a continuation of application Ser. No. 09/951,362 filed Sep. 13, 2001, now abandoned which is a divisional of application Ser. No. 09/310,891 filed May 12, 1999 (now U.S. Pat. No. 6,309,417), the disclosures of which are fully incorporated herein by reference.

FIELD OF THE INVENTION

The present invention generally relates to heart valve replacement and, more particularly, to replacement heart valves and apparatus used during their implantation.

BACKGROUND OF THE INVENTION

A popular option for aortic valve replacement is to retain the native aortic root and the normal coronary artery attachments and secure the replacement prosthesis inside the patient's own aorta. With this procedure, only the valve is replaced and not the entire root. It is unnecessary to re-attach the coronary arteries and, should repeat surgery be necessary, a surgeon must only replace the valve and not an entire section of the aorta. When a surgeon replaces the aortic valve in this manner, the patient is first placed on a heart-lung machine and the section of the aorta having the aortic valve is clamped off to allow access. That section of the aorta is therefore collapsed and unpressurized leaving a pressurized section connected to the heart-lung machine. The unpressurized section of aorta is then opened and the diseased valve is removed in its entirety, including careful removal of calcium deposits within the aorta and annulus. The aorta and sinotubular junction are then sized and the surgeon prepares the appropriate replacement valve. The surgeon then sutures the inflow or annular end of the replacement valve into the inside of the aorta. When these sutures are drawn tight, the valve is pulled inside the aorta when approximately 20 sutures are then applied around the annular end. The commisures of the replacement valve, which extend from the annular end, may or may not need to be affixed to the aorta as discussed below.

Two major types of prosthetic or replacement heart valves exist. The first general type of valve is a mechanical prosthesis which includes commisures that are self-supporting and do not need to be affixed to the aortic wall. Mechanical prostheses are generally formed entirely of artificial material, such as carbon fiber, titanium, dacron and teflon. While these mechanical prostheses are durable, relatively quick to implant and generally easy to manipulate during surgery, they also have certain disadvantages. For example, due to the artificial materials used in their construction, blood clots can form on the valve and subsequently cause valve failure. If the clot dislodges from the valve, the clot can lodge in a downstream vessel and cause stroke or organ ischemia. For these reasons, patients with mechanical heart valves must take anticoagulants for the rest of their lives. Anticoagulants bring about their own complications in some patients, including internal bleeding or other side effects.

The second major type of prosthetic or replacement heart valve is a biologic valve. This category includes valves harvested from human cadavers, i.e., allografts or homografts, or animal tissue generally harvested from cows and pigs. More recently, there has been increasing effort to develop synthetic biologically compatible materials to substitute for these natural tissues. Among their advantages, biologic prostheses generally do not require lifelong anticoagulation as they do not often lead to clot formation. These valves are provided in stented or unstented forms. A stented valve includes a permanent, rigid frame for supporting the valve, including the commisures, during and after implantation. The frames can take the form of a wire or other metal framework or a plastic frame encased within a flexible fabric covering. Unstented valves do not have built-in commisure support so surgeons must use their skill and best judgement to determine the optimal site of implantation inside the patient's native aorta to maintain valve competence. When securing the valve commisures, obstruction of the patient's native coronary arteries must be avoided or myocardial infarction may result.

There are many limitations to procedures utilizing permanently stented biologic replacement valves. First, allografts (human cadaver donor valves) are not generally available with permanent frames or stents. Second, the frames or stents can take up valuable space inside the aorta such that there is a narrowing at the site of valve implantation. This narrowing leads to pressure gradients and increased loads on the left ventricle and, therefore, increased incidence of hypertrophy and reduced patient survival. The frame includes artificial materials which can increase the risk of new infection or perpetuate an existing infection. It is also very important to realize that although the permanent frames or stents guarantee alignment of the commisures, they cause very high stresses on the commisures when the valve cusps move between open and closed positions. A patient's natural commisures are not placed under significant strain during opening and closing of the valve due to the natural resilience of the aorta. On the other hand, artificially mounted valves place the commisures under strain during operation of the valve due to the rigid materials of the frame. Over time, the valve cusps tend to decay under this strain and manifest calcification and tears which can lead to valve failure.

In many situations, biologic replacement heart valves are preferred in the unstented form due to the drawbacks mentioned above. Such valves are more resistant to infection when implanted free of any foreign material attachments, such as stents or frames. Also, the heart valve is more efficient when used without a stent. Efficiency refers to the pressure gradient across the valve during use. Natural human valves have almost no pressure gradient. When a natural heart valve is replaced by a biologic heart valve with a low pressure gradient, complications such as hypertrophy arise less often and result in improved patient survival.

Despite the known advantages of using biologic prosthetic heart valves without artificial supporting devices such as permanent stents or frames, relatively few surgeons employ this surgical technique due to its high level of difficulty. When unsupported or unstented by artificial devices, such as permanent stents, biologic replacement heart valves have a flimsy, soft and flexible nature. That is, the commisures of the heart valve do not support themselves in the proper orientation for implantation. For these reasons, it is very difficult to secure the commisures properly into place. In this regard, the surgeon must generally suture the individual commisures of the heart valve in exactly the proper orientation to allow the valve to fully and properly function.

During valve replacement surgery, an L-shaped retractor is placed inside the aorta to pull it open for access purposes. While this provides exposure, it distorts the aorta and may give the surgeon an incorrect impression of the correct valve position. Next, and especially with regard to unstented biologic valve procedures, the surgeon must guarantee that the commisures pass straight up the aorta at roughly right angles to the plane of the annulus. There is very little technology to help the surgeon correctly place the stentless replacement valve. To help confirm that the leaflets are correctly spaced at 120° apart, surgeons may use a disc having markings 120° apart. The surgeon can use this to roughly estimate the spacing by placing it near the distal ends of the commisures. However, this provides only a rough guide. For example, it is possible to equally space the commisures at the upper end and still have a valve placed in a skewed position. Finally, the aorta is not a straight tube at the surgical site, but instead flares outward at the surgical site. The valve must conform to the flare of the aorta at this location. Once the surgeon has completed an inspection for these three elements, i.e., correct spacing at approximately 120° between the commisures, correct perpendicular position of the commisures relative to the annulus plane, and appropriate conformation to the flare of the aorta, the surgeon must suture the commisures to the wall of the aorta. As this is done, it is necessary to make sure there is no encroachment on the ostia or origins of the coronary arteries. After the valve commisures are attached to the aorta and proper orientation and positioning is confirmed, the surgeon closes the aorta.

Following surgery, there is a risk that the aorta will dilate at the sinotubular junction months or years later and draw the valve commisures and attached cusps apart from each other. This will cause insufficiency and failure due to leakage through the valve. There is a further need for methods to ensure that late enlargement of the sinotubular junction does not necessitate reoperation for late valve insufficiency and failure.

In general, there is an increasing need for devices which improve the efficiency and reliability of implanting replacement heart valves. In conjunction with this, there is a need to improve these procedures so that all surgeons, not just those with the highest skill levels, can implant heart valves with superior results.

SUMMARY OF THE INVENTION

The present invention generally provides apparatus directed at solving problems, such as those described above, with regard to replacing a heart valve within a vessel. In one general aspect, the invention provides a replacement heart valve and a plurality of temporary commisure stabilizers. More particularly, the replacement heart valve will generally have an annular base and a plurality of spaced apart commisures extending from the annular base at spaced apart positions. The valve may be formed of animal tissue, such as valves harvested from pigs, cows or human donors. Optionally, the valve may be formed from synthetic, biologically compatible material. With the typical aortic valve replacement, there will be three commisures spaced roughly 120° apart. Each commisure includes a proximal end connected with the annular base and an opposite distal end. The plurality of commisure stabilizers are connected to the commisures in a removable manner. These commisure stabilizers position and stabilize the commisures of the replacement heart valve as a surgeon secures the replacement heart valve in place within the vessel. The commisure stabilizers, in the instance of an aortic valve replacement, positively orient the commisures at the 120° spaced apart positions and generally perpendicular to a plane which contains the annular base of the heart valve.

Following securement of the replacement heart valve within the vessel, the commisure stabilizers are preferably removed to avert the various disadvantages of permanent stents or frames. However, there may be situations in which a particular surgeon desires to leave one or more of the commisure stabilizers in place and the invention advantageously provides for this option as well. In the preferred embodiment, the commisure stabilizers are connected together at spaced apart distal positions, for example, by a generally annular member. Each commisure stabilizer preferably comprises at least one elongate member attachable in a manner allowing removal from the distal end of the respective commisure following implantation of the heart valve.

The replacement heart valve can include respective receiving elements for the commisure stabilizers. These may comprise pockets, loops or other structure adapted to receive the stabilizers in a manner allowing removal by a surgeon at the distal end of the commisures after implantation. The commisure stabilizers may also be removably affixed to other supporting structure, such as the generally annular member described above. This, for example, will allow the surgeon to remove the annular member or other supporting structure for easier suturing access, while at least temporarily leaving the commisure stabilizers in place for positioning purposes. After suturing and/or other securement of the valve, the commisure stabilizers would be removable to achieve the full advantages of this invention.

Each commisure stabilizer may further comprise at least two spaced apart elongate members or, more preferably, three elongate members. One or more of these members may curve or flare outwardly in a lengthwise direction to urge the commisures of the replacement heart valve against the flared interior wall of the vessel. The outer elongate members may also angle or curve away from the central elongate member to extend along opposite edge portions of the respective commisures.

In another aspect of the invention, the positioning and stabilizing device may be formed in a collapsible manner allowing insertion into the vessel in a collapsed state and subsequent expansion for positioning and stabilizing the valve commisures during securement of the valve within the vessel. For example, the positioning and stabilizing device may be at least partially formed of a shape memory material allowing the positioning device to be collapsed and expanded as necessary. This aspect of the invention may also be practiced in other manners, such as through the use of hinged or otherwise collapsible and expandible structures.

In accordance with another aspect of the invention, a flexible material may connect the distal ends of the three commisures. This will prevent the commisures from moving radially apart due to late sinotubular enlargement. This material may also be secured to the internal wall of the vessel to help prevent the need for reoperation due to the complications of late enlargement of the sinotubular junction as described above.

A method of implanting a replacement heart valve in accordance with the invention includes inserting the replacement heart valve into a patient, connecting at least one commisure stabilizer to each of the commisures of the replacement heart valve either before or after inserting the replacement heart valve, securing the replacement heart valve within the patient using the commisure stabilizers to orient the commisures of the replacement heart valve, and removing one or more of the commisure stabilizers from the patient leaving the secured replacement heart valve in place. Other methods of utilizing apparatus as described herein are also within the scope of this invention as will be apparent.

These and other objects, advantages, and features of the invention will become more readily apparent to those of ordinary skill in the art upon review of the following detailed description of the preferred embodiments, taken in conjunction with the accompanying drawings and as more generally set forth in the appended claims.

BRIEF DESCRIPTION OF THE DRAWINGS

FIG. 6 is a perspective view of another alternative positioning and stabilizing device constructed in accordance with the invention;

FIG. 6A is a cross sectional view taken along line 6A—6A of FIG. 6;

FIG. 7 is a perspective view of another alternative embodiment of a positioning and stabilizing device;

FIG. 9 is a perspective view of an alternative replacement heart valve and removable positioning and stabilizing device constructed in accordance with the invention;

FIG. 9A is a perspective view of the apparatus shown in FIG. 9 with the positioning and stabilizing device removed;

FIG. 9B is a fragmented and enlarged view of the positioning and stabilizing device of FIGS. 9 and 9A showing the separable parts thereof;

DETAILED DESCRIPTION OF THE PREFERRED EMBODIMENTS

Figure 1:
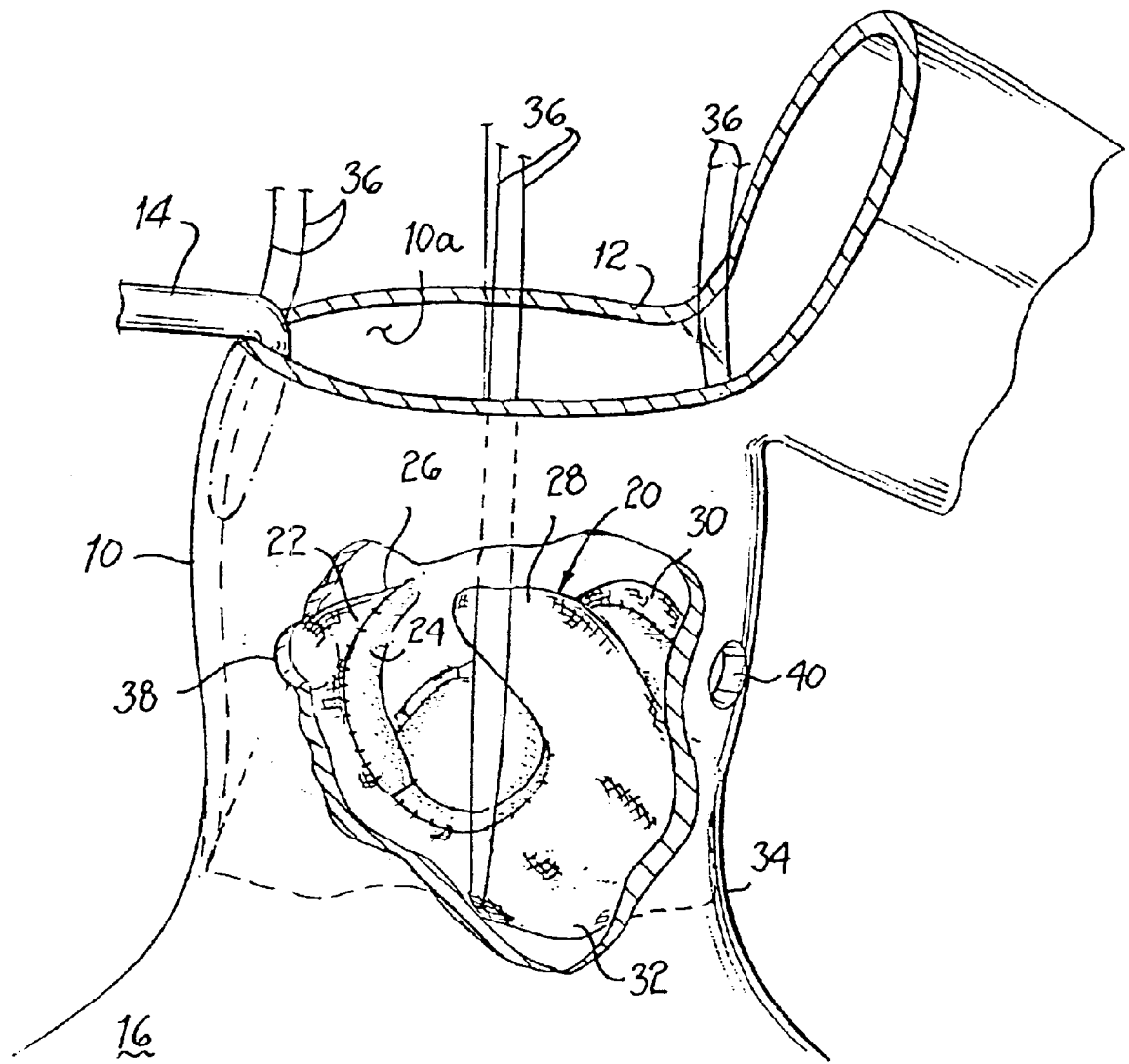
FIG. 1 is a partially fragmented perspective view of an aorta undergoing a valve replacement operation with an unstented biologic replacement valve in the process of insertion.

FIG. 1 illustrates an aorta 10 which a surgeon has incised to create an opening 12 after a patient has been placed on a heart-lung machine. One or more retractors 14 may be used by assistants to gain access to opening 12. Aorta 10 may be partially incised as shown or it may be fully incised across its transverse dimension. During this procedure, the patient's heart 16, disposed below the surgical site, is normally in an arrested state due to the use of the heart-lung bypass machine and cardioplegia.

An unstented replacement valve 20 is further shown within aorta 10 in an initial flimsy, unsupported condition. In this case, a fabric covering 22 is stitched on the outside of the biologic tissue 24, which may be human or other animal tissue or synthetic material. Replacement valve 20 comprises typically three commisures 26, 28, 30 extending from an annular base 32. Replacement valve 20 has been inserted within aorta 10 such that annular base 32 is disposed at the annulus 34 of aorta 10. Conventional sutures 36 may be used as shown to pull replacement valve 20 within aorta 10 until it resides on annulus 34 in a known manner.

Figure 2:
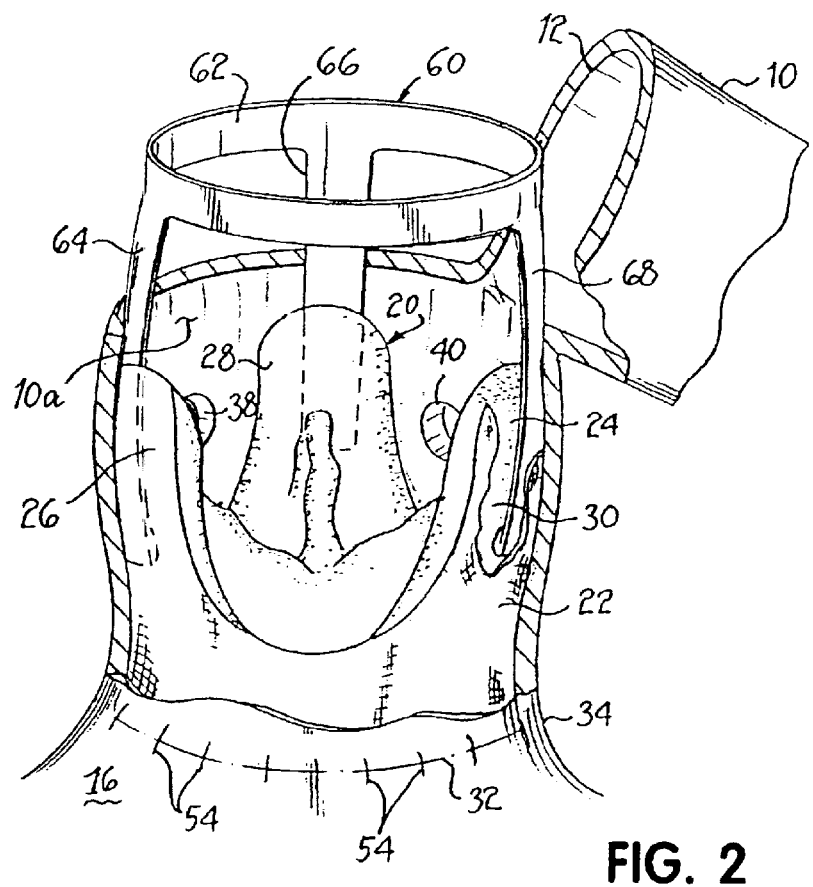
FIG. 2 is a view similar to FIG. 1, but showing the initial removable attachment of a positioning and stabilizing device having commisure stabilizers constructed in accordance with one embodiment of the invention.
Figure 4:
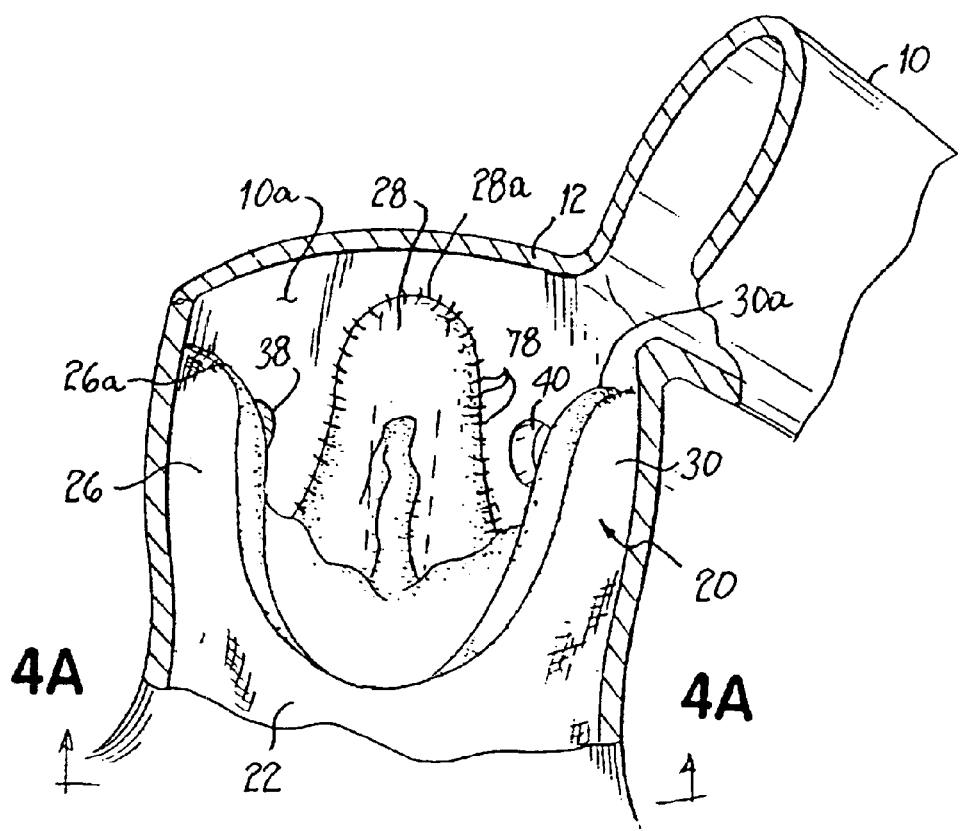
FIG. 4 is a perspective view similar to FIG. 3, but showing the fully implanted heart valve.
Figure 4A:
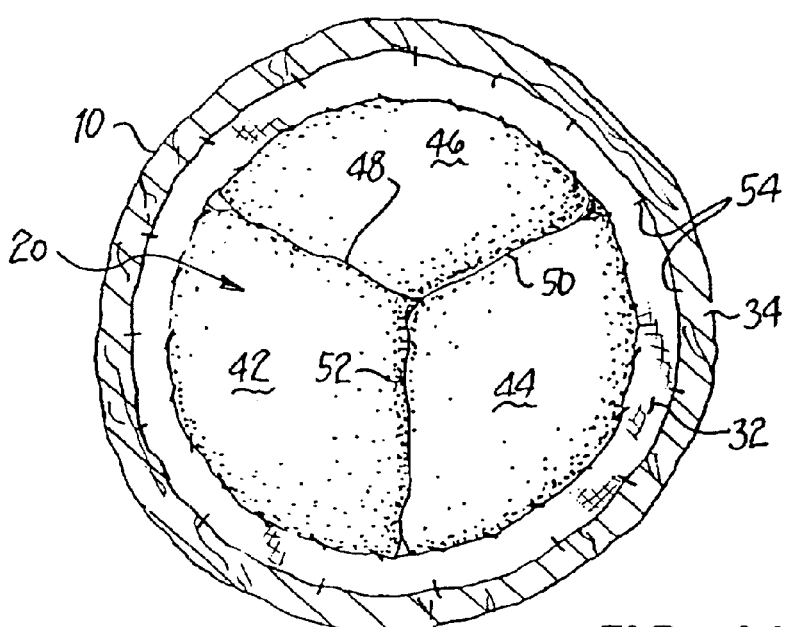
FIG. 4A is a cross sectional view taken along line 4A—4A of FIG. 4.

As further shown in FIG. 4A, a plurality of sutures 54 are typically placed around the annular base 32 and into annulus 34. Replacement valve 20 must be disposed within aorta 10 so as not to occlude orifices 38, 40 communicating with the left and right coronary arteries (FIG. 2). As additionally shown in FIG. 4A, the typical aortic replacement valve includes three cusps 42, 44, 46, respectively connected with the three commisures 26, 28, 30 for movement between open and closed positions as the heart beats to pump blood into the aorta. Sealing lines of contact 48, 50, 52 are formed between the respective cusps 42, 44, 46. To maintain an effective seal along lines 48, 50, 52, commisures 26, 28, 30 must be positioned and secured within aorta 10 in a precise manner. In this regard, each commisure should preferably extend in a relatively perpendicular, non-skewed manner along the interior aortic wall 10a, and in a manner that is essentially perpendicular to annular base 32. If this is not done, strain will be placed on commisures 26, 28, 30 and an effective seal between cusps 42, 44, 46 may eventually be lost. Undue strain on commisures 26, 28, 30 can cause decay and calcification and eventually lead to valve failure and either death or a second surgical operation.

Figure 3:
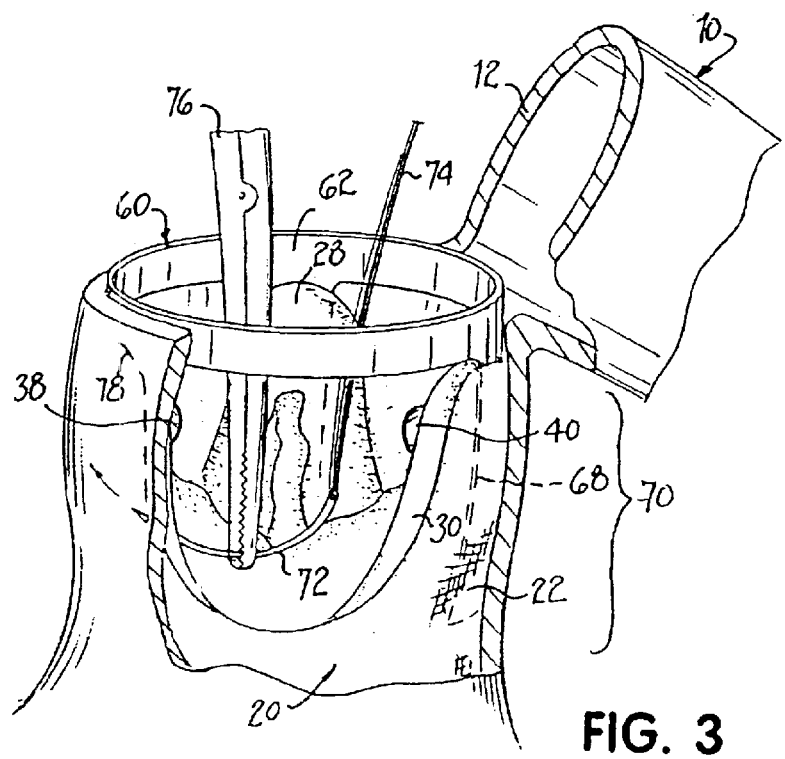
FIG. 3 is a perspective view similar to FIG. 2, but showing the positioning and stabilizing device fully inserted and the properly positioned and stabilized commisures being sutured in place.

FIGS. 2 and 3 illustrate one embodiment of a positioning and stabilizing device 60 constructed in accordance with the invention. Generally, positioning and stabilizing device 60 may be used in a temporary manner while securing commisures 26, 28, 30 to aortic wall 10a. Positioning and stabilizing device 60, in this embodiment, includes an annular portion 62 connected with a plurality of stabilizers 64, 66, 68, each taking the form of a single elongate member. Each stabilizer 64, 66, 68 preferably bows outwardly along its length so as to generally conform to a flared region 70 of the aortic root. As one of many possible temporary securement methods, each stabilizer 64, 66, 68 is slipped between fabric covering 22 and biologic tissue 24 of replacement valve 20. In the case of a valve which does not have a fabric covering, other securing structure such as suture loops, hooks, etc., may be used to attach stabilizers 64, 66, 68. This temporary connection may be made before replacement valve 20 is inserted into aorta 10 or after valve 20 is inserted within aorta 10. In the preferred embodiments, assembly of a positioning and stabilizing device and replacement valve, such as device 60 and valve 20, is felt to be best accomplished prior to surgery to allow for insertion as a unit. As shown in FIG. 3, once replacement valve 20 and positioning and stabilizing device 60 have been secured within aorta 10, with stitches 54 already placed at annulus 34, suturing of commisures 26, 28, 30 can begin. This may be accomplished using a typical needle 72 and suturing thread 74 manipulated by a gripping implement 76. The surgeon places sutures 78 in this manner along the entire periphery of each commisure 26, 28, 30. It will be appreciated that other manners of securing replacement valve 20 to aorta 10 may be used in accordance with the invention and, for example, include gluing, stapling or other mechanical fasteners. FIG. 4 illustrates the completely secured replacement valve 20 implanted within aorta 10. It will be appreciated that, in this embodiment, once positioning and stabilizing device 60 has been removed from the pockets formed between fabric covering 22 and biologic tissue 24, the distal ends 26a, 28a 30a may be stitched to the aortic wall 10a.

Figure 5:
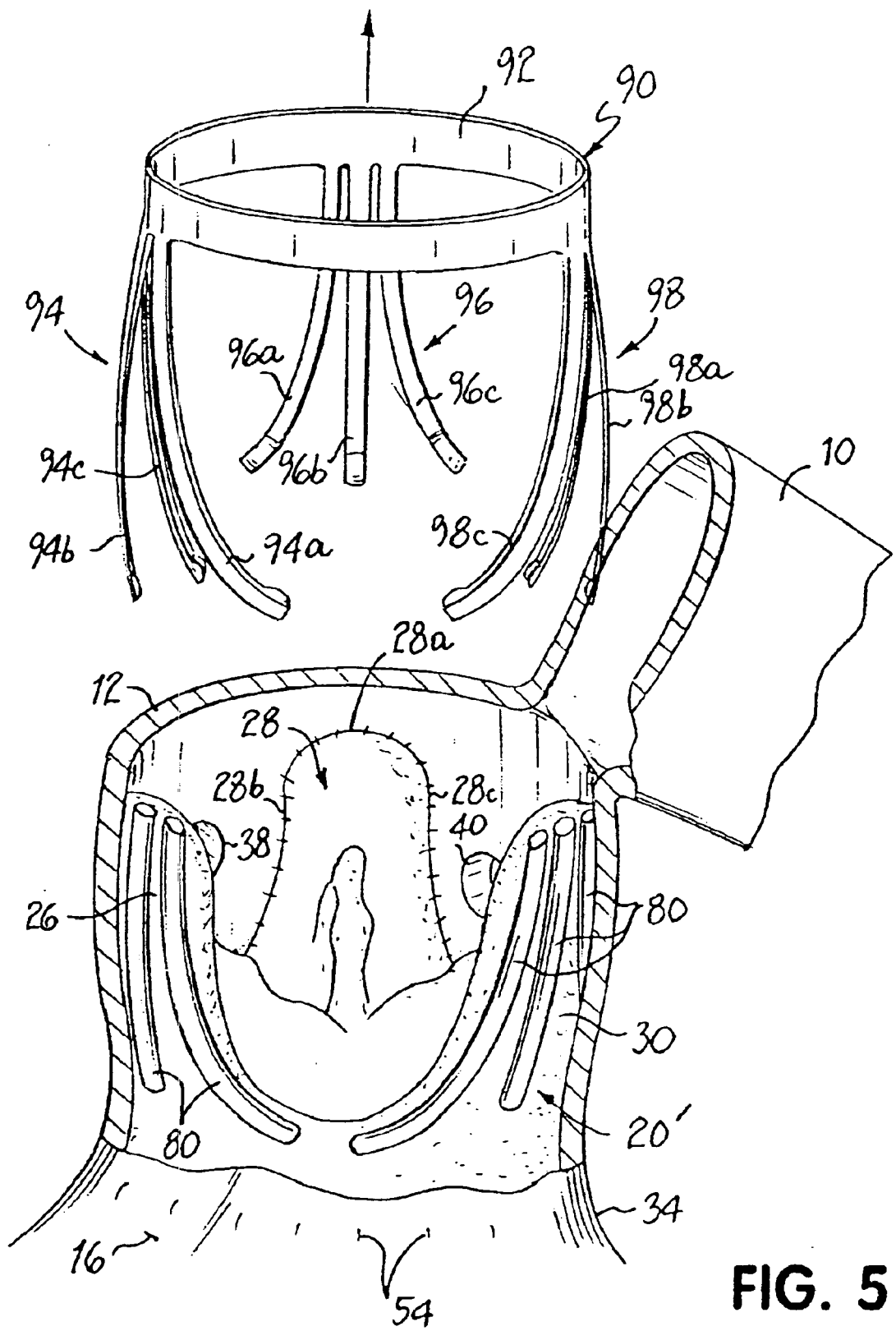
FIG. 5 is a perspective view showing an alternative embodiment of a positioning and stabilizing device being removed from a replacement heart valve following implantation.

FIG. 5 illustrates one alternative embodiment of a replacement valve 20' useful in accordance with the invention. Replacement valve 20 includes pockets 80 on the outside of each commisure 26, 28, 30 for receipt of an alternative positioning and stabilizing device 90. Like the first embodiment, positioning and stabilizing device 90 can include an annular portion 92 and a plurality of three stabilizers 94, 96, 98. In this embodiment, each stabilizer further comprises multiple elongate members adapted to be removably inserted within pockets 80. More specifically, each stabilizer 94, 96, 98 comprises respective elongate members 94a–c, 96a–c and 98a–c. As will be appreciated from stabilizer 96, outer elongate members 96a, 96c curve outwardly from the middle elongate member 96b. In this manner, outer members 96a, 96c extend within respective pockets 80 along the outer curved edges 28b, 28c of commisure 28. The remaining stabilizers 94, 98 function in a similar manner. It will be further appreciated that each stabilizer 94, 96, 98 bows outwardly, as in the first embodiment, to conform to the flare 70 at the aortic root. Stabilizers 94, 96, 98 are flexible enough to be withdrawn, as shown in FIG. 5, from pockets 80 after suturing of each commisure 26, 28, 30 as previously described. Positioning and stabilizing device 90 may be formed from various materials and in various configurations for this purpose. These may include metals, super elastic alloys, or plastics.

FIGS. 6 and 6A illustrate another alternative positioning and stabilizing device 100 constructed in accordance with the invention. In this embodiment, an annular portion 102 is removable from a plurality of commisure stabilizers 104, 106, 108. In this manner, positioning and stabilizing device 100 may be used as described above with respect to devices 60 and 90, except that annular portion 102 may be removed for easier suturing access or other securement access when securing commisures 26, 28, 30 (FIG. 4) to aortic wall 10a. One of many possibilities for facilitating this function is shown in FIG. 6 and FIG. 6A in the form of connectors 110, 112, 114. Each of these connectors may receive a stabilizer 104, 106, 108 in a removable fashion with a slight interference fit. As best shown in FIG. 6A, an end portion 104a of stabilizer 104 may be received with a slight interference fit against a resilient tab 116. The other stabilizers 106, 108 may have a similar structure, as exemplified by end 108a shown in FIG. 6. Many other fastening structures are possible other than this schematically illustrated example.

FIG. 7 illustrates another alternative positioning and stabilizing device 120 having a generally similar construction and function to device 90 shown in FIG. 5. Device 120 may be formed from a single length of wire, for example, and includes portions 122, 124, 126 analogous to the previously described annular portions. A connector 128 may be provided to connect opposite ends of the wire. Stabilizers 130, 132, 134 are formed with three sections each for purposes previously described in connection with FIG. 5. These sections 130a–c, 132a–c, 134a–c serve similar functions to position and stabilize the commisures of a replacement heart valve, and device 120 may be removed from the heart valve in previously described manners.

Figure 8A:
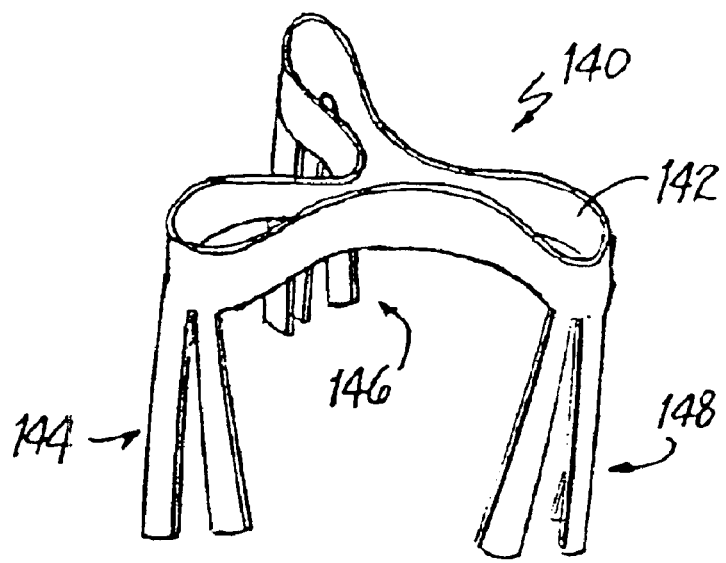
FIGS. 8A and 8B are perspective views of another alternative positioning and stabilizing device respectively shown in collapsed and expanded conditions.
Figure 8B:
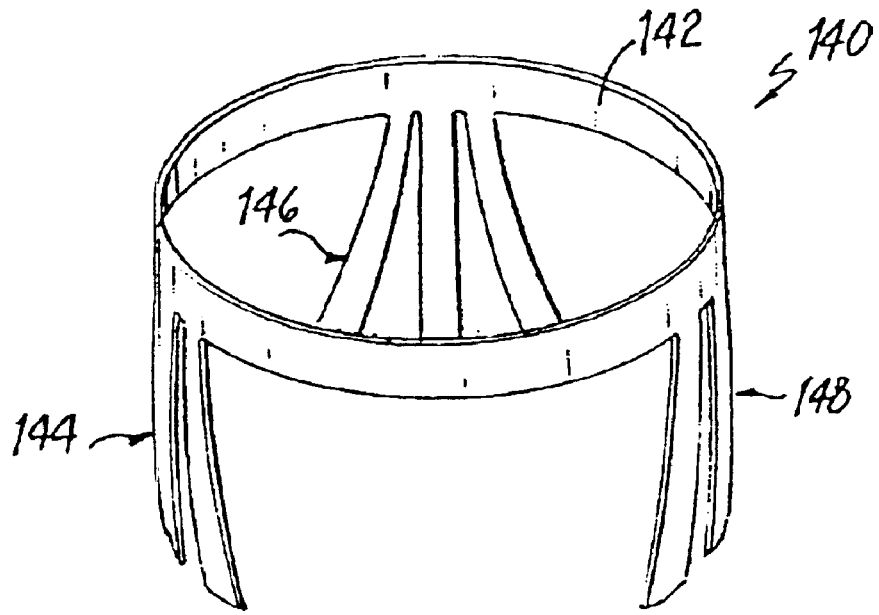

FIGS. 8A and 8B illustrate another alternative positioning and stabilizing device 140 constructed from a shape memory material such as Nitenol. As shown in FIG. 8A, device 140 may be collapsed in each a detached form with respect to a heart valve, as shown, or while connected to a replacement heart valve for insertion within the patient's aorta as a unit. Upon the application of heat or electric current once inserted within the aorta, device 140 expands to the position shown in FIG. 8B and may then be used as previously described to position and stabilize the heart valve commisures during implantation. As shown in FIGS. 8A and 8B, one illustrative example of this device also includes an annular portion 142 and respective three-legged commisure stabilizers 144, 146, 148.

FIGS. 9 and 9A illustrate another heart valve replacement apparatus 160 constructed in accordance with the invention. In this embodiment, a replacement heart valve 162 may include a flexible material 164, optionally part of the fabric covering 166 of valve 162, which secures the three commisures 168, 170, 172 together at their respective distal ends 168a, 170a, 172a. It will be appreciated that flexible material 164 may be stitched to the interior aortic wall in conjunction with commisures 168, 170, 172. Thus, material 164 will prevent distal ends 168a, 170a, 172a from expanding away from one another as occurs during late sinotubular enlargement of the aorta. Therefore, this prevents valve failure as a result.

As further shown in FIGS. 9, 9A and 9B, an alternative embodiment of a positioning and stabilizing device 180 includes an annular portion 182 constructed from separate sections 182a, 182b, 182c, and a plurality of three stabilizers 184, 186, 188. Stabilizer 184, 186, 188 again are shown as three-legged structures for purposes previously described. In this embodiment, however, stabilizers 184, 186, 188 are retained within loops 190, which may be suture loops sewn into fabric 166. It will be appreciated that other types of retaining structure may be used to at least temporarily retain stabilizers 184, 186, 188. In this embodiment, connectable end portions 192, 194, formed respectively as male and female portions, may be used to make various connections and disconnections on device 180. For example, lower ends of adjacent stabilizers 184, 186, 188 may be connected at a junction 196 as shown in FIG. 9. This may provide more consistent support along the edges of commisures 168, 170, 172. As further shown in FIG. 9B, stabilizers 184, 186, 188 may be completely disconnectable from annular portion 182 while also allowing selective disconnection of sections 182a, 182b, 182c. This may be accomplished through the use of connecting elements 198 having respective female connecting portions 198a for engaging male connecting portions 192. It will be understood that many alternative connectors and structures may be substituted for those shown while retaining the basic function and general concepts expressed herein.

Figure 10:
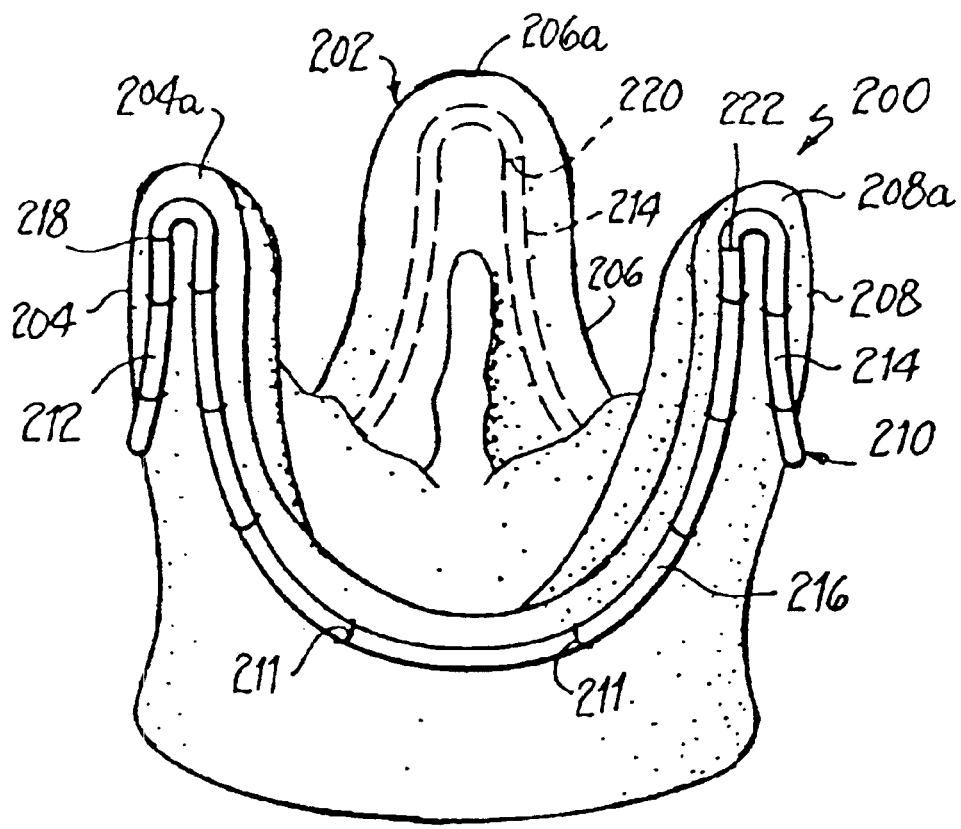
FIG. 10 is a perspective view of another alternative replacement heart valve and removable positioning and stabilizing device constructed in accordance with the invention.

FIG. 10 illustrates a heart valve replacement apparatus 200 comprised a replacement heart valve 202, which may be formed from biological tissue or synthetic biologically compatible material. Heart valve 202 is again illustrated with three commisures 204, 206, 208, as is typical for replacement aortic valves. A positioning and stabilizing device 210 is fastened to the outside of valve 202, for example, by suture loops 211. This embodiment of the invention does not have any connection between the distal ends 204a, 206a, 208a of commisures 204, 206, 208 or at the distal end of positioning and stabilizing device 210. Also, in this embodiment positioning and stabilizing device 210 is formed in three sections 212, 214, 216 removably connected together at junctions 218, 220, 222. These connections may be similar to those shown in FIG. 9B. Other types of connections may be used as well. Use of this embodiment of the invention will be similar to the previous embodiments, except that sections 212, 214, 216 may be removed individually from heart valve 202 following completion of its securement within the aorta. Sections 212, 214, 216 are preferably formed of a highly flexible plastic or metal which is biocompatible. This embodiment provides certain advantages, such as allowing one or more of the sections 212, 214, 216 to remain in place following surgery and providing additional room for a surgeon to access commisures 204, 206, 208 while suturing or otherwise securing commisures 204, 206, 208 to the aortic wall. It will be appreciated that other configurations and numbers of legs and sections may be utilized by those of ordinary skill.

Figure 11:
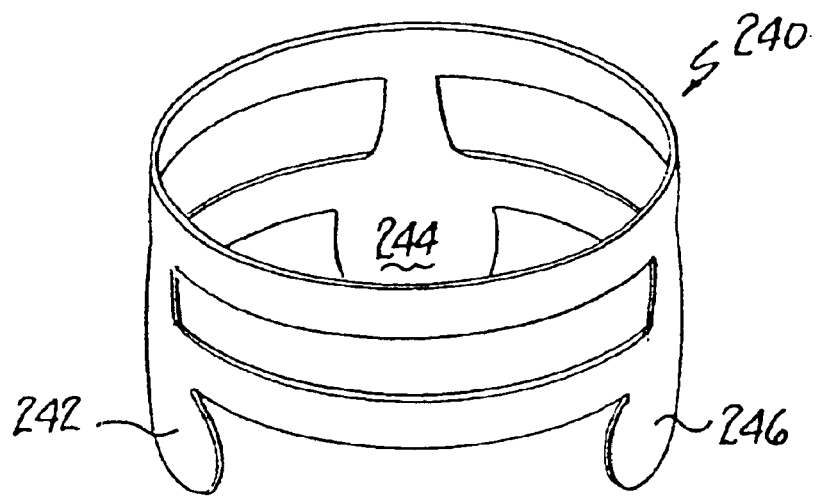
FIG. 11 is a perspective view of an aortic expansion device constructed in accordance with the invention.

FIG. 11 illustrates an expansion device 240 useful for expanding a vessel, such as the aorta, during valve replacement procedures. In this embodiment, expansion device may be formed as a collapsible and expandable structure, such as by being formed of shape memory material as described with respect to FIGS. 8A and 8B. It will be appreciated that FIG. 11 shows the expanded condition only. Expansion device 240 may have three extensions 242, 244, 246 of a desired length for disposition between the respective commisures of an aortic replacement valve. Device 240 need not be attached to heart valve commisures, but may be used to expand the collapsed aorta to the proper flared shape thereby assisting the surgeon during a heart valve replacement procedure. This device overcomes the drawbacks of typical retractors which tend to distort the shape of the collapsed aorta and mislead the surgeon as to the correct position and orientation of the heart valve. Device 240 may be formed in various manners to be collapsible and selectively expandable, such as through the use of mechanically expandable portions or, preferably, expandable shape memory portions.

Figure 12:
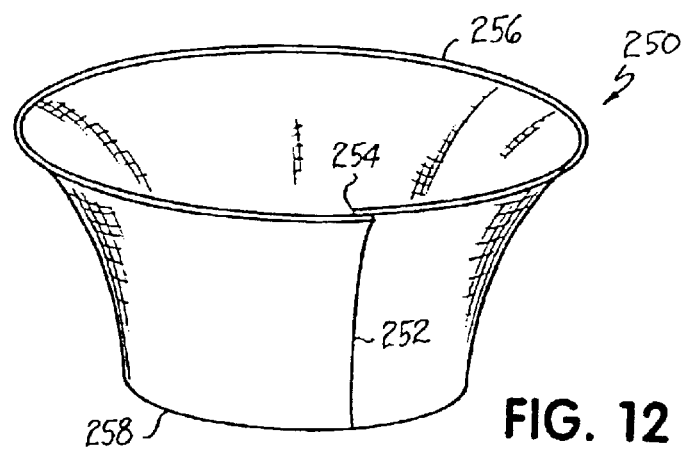
FIG. 12 is a perspective view of an alternative aortic expansion device.
Figure 13A:
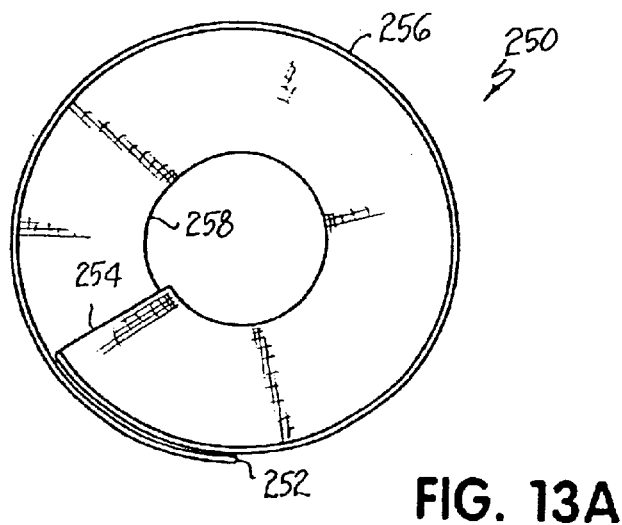
FIG. 13A is a top view of the expansion device illustrated in FIG. 12, but shown in a collapsed condition.
Figure 13B:
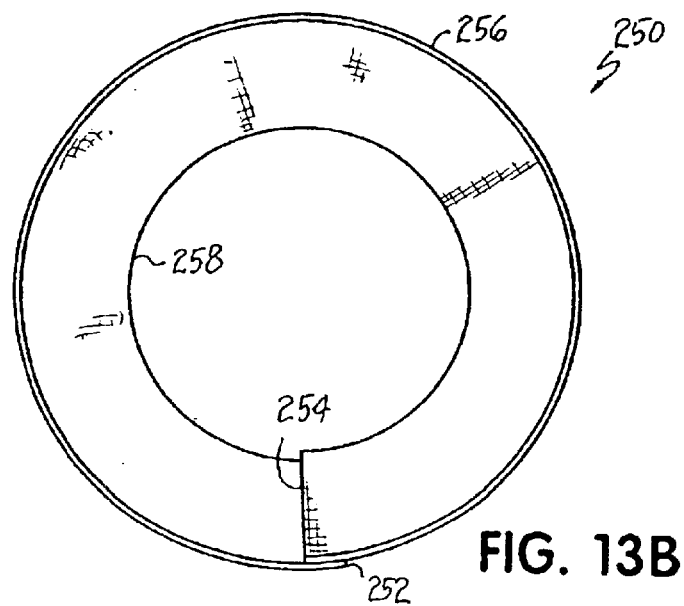
FIG. 13B is a top view of the expansion device shown in FIG. 12 in an expanded condition.

FIGS. 12, 13A and 13B illustrate an alternative collapsible and expandable retraction device 250. This device may be formed from a mesh or screen material and includes edge portions 252, 254 which allow expanding and contracting of the device. An upper end 256 is formed with a greater diameter than a lower end 258 in the expanded, operative position shown in FIGS. 12 and 13B. This allows a surgeon to have greater access into and through the device to manipulate and, for example, suture a replacement heart valve in place below device 250 within the aorta. In use, and referring back to FIG. 1, a surgeon will insert the device 250 in the collapsed form shown in FIG. 13A through opening 12 such that lower end 258 is situated within aorta 10 and upper end 256 is exposed. The surgeon will then allow device 250 to expand through its own resilience or through a shape memory property to the position shown in FIG. 13B. Alternatively, other activation structure or means may be provided for attaining the expanded condition. Once expanded, aorta 10 generally assumes a natural, pressurized shape allowing placement and implantation of replacement valve 20 in a more efficient and accurate manner. It will be understood that the expansion devices shown in FIGS. 11 through 13B are illustrated in the simplest currently contemplated forms. It is further contemplated that additional handles or other support and actuation structure may be added while achieving the same general advantages of these embodiments.

While the present invention has been illustrated by a description of a preferred embodiment and while this embodiment has been described in some detail, it is not the intention of the Applicants to restrict or in any way limit the scope of the appended claims to such detail. Additional advantages and modifications will readily appear to those skilled in the art. The various features and concepts of the invention may be used alone or in numerous combinations depending on the needs and preferences of the user. This has been a description of the present invention, along with the preferred methods of practicing the present invention as currently known. However, the invention itself should only be defined by the appended claims, wherein we claim.

What is claim is:

1. A method of implanting a replacement heart valve including an annular base and a plurality of commisures extending from spaced apart positions of the annular base, the method comprising:

inserting the replacement heart valve into a patient, connecting at least one commisure stabilizer to each of the commisures of the replacement heart valve either before or after inserting the replacement heart valve, leaving a central opening between the commisure stabilizers sufficiently sized to introduce a suturing implement therethrough, suturing the commisures to the patient by introducing the suturing implement through the central opening and using the commisure stabilizers to orient the commisures of the replacement heart valve, and removing at least a portion of the commisure stabilizers from the patient leaving the secured replacement heart valve in place within the patient.

2. A method of implanting a replacement heart valve including an annular base and a plurality of commisures extending from spaced apart positions of the annular base, the method comprising:

connecting three commisure stabilizers of a positioning and stabilizing device to the respective three commisures of the replacement heart valve, inserting the replacement heart valve and the connected commisure stabilizers into a patient, leaving a central opening between the commisure stabilizers sufficiently sized to introduce a suturing implement therethrough, suturing the commisures to the patient by introducing the suturing implement through the central opening and using the commisure stabilizers to orient the commisures of the replacement heart valve, and removing at least a portion of the commisure stabilizers from the patient leaving the secured replacement heart valve in place within the patient.

3. A method of implanting a replacement heart valve including an annular base and a plurality of commisures extending from spaced apart positions of the annular base, the method comprising:

inserting the replacement heart valve into a patient, connecting at least one commisure stabilizer to each of the commisures of the replacement heart valve either before or after inserting the replacement heart valve, securing the commisures to the patient while using the commisure stabilizers to orient the commisures of the replacement heart valve, and removing only a portion of the commisure stabilizers from the patient while leaving a remaining portion thereof and the secured replacement heart valve in place within the patient.

* * * * *